US007463918B2

(12) United States Patent
Kim et al.

(10) Patent No.: US 7,463,918 B2
(45) Date of Patent: Dec. 9, 2008

(54) METHOD AND APPARATUS FOR RECEIVING DATA IN HUMAN BODY COMMUNICATION SYSTEM

(75) Inventors: Tae-Song Kim, Seoul (KR); Jong-Oh Park, Seoul (KR); Byung-Kyu Kim, Seoul (KR); Jin-Seok Kim, Seoul (KR); Han Cheung, Daejeon (KR); Won-Woo Cho, Daejeon (KR); Nan-Young Yoon, Daejeon (KR); Young-Rok Kim, Deajeon (KR)

(73) Assignee: Korea Institute of Science and Technology (KR)

( * ) Notice: Subject to any disclaimer, the term of this patent is extended or adjusted under 35 U.S.C. 154(b) by 419 days.

(21) Appl. No.: 10/543,231

(22) PCT Filed: Dec. 31, 2003

(86) PCT No.: PCT/KR03/02938

§ 371 (c)(1),
(2), (4) Date: Jul. 22, 2005

(87) PCT Pub. No.: WO2004/066833

PCT Pub. Date: Aug. 12, 2004

(65) Prior Publication Data
US 2006/0173265 A1 Aug. 3, 2006

(30) Foreign Application Priority Data
Jan. 25, 2003 (KR) .................... 10-2003-0005058

(51) Int. Cl.
*A61B 5/05* (2006.01)

(52) U.S. Cl. ............... 600/407; 600/300; 600/101
(58) Field of Classification Search ............... 600/476, 600/473, 407, 547, 101, 300; 340/870.11, 340/573.1; 128/899
See application file for complete search history.

(56) References Cited

U.S. PATENT DOCUMENTS

| 4,278,077 | A |   | 7/1981 | Mizumoto ............... 128/4 |
| 5,604,531 | A |   | 2/1997 | Iddan et al. ............... 348/76 |
| 5,951,483 | A | * | 9/1999 | Joo ............... 600/509 |
| 6,240,312 | B1 |   | 5/2001 | Alfano et al. ............... 600/476 |
| 6,301,500 | B1 | * | 10/2001 | Van Herk et al. ............... 607/2 |
| 6,314,315 | B1 | * | 11/2001 | Hung et al. ............... 600/547 |
| 6,343,140 | B1 | * | 1/2002 | Brooks ............... 382/115 |
| 6,351,666 | B1 | * | 2/2002 | Cuzick et al. ............... 600/547 |

FOREIGN PATENT DOCUMENTS

KR 2002-89669 A 11/2002
KR 2003 89223 A 11/2003

OTHER PUBLICATIONS

International Search PCT/2003/002938 dated Apr. 28, 2004.

* cited by examiner

*Primary Examiner*—Eric F Winakur
*Assistant Examiner*—Katherine L Fernandez
(74) *Attorney, Agent, or Firm*—McNeely Bodendorf LLP

(57) ABSTRACT

The present invention provides a method and apparatus for receiving data in a human body communication system. The receiving apparatus, which comprises plural receiving electrodes, selects the optimum pair of receiving electrodes when receiving data, so that it can improve quality of received information and obtain position information of a sensor in the human body.

12 Claims, 3 Drawing Sheets

METHOD AND APPARATUS FOR RECEIVING DATA IN HUMAN BODY COMMUNICATION SYSTEM

CROSS REFERENCE TO RELATED APPLICATION

The present application is a 35 U.S.C. § 371 national phase conversion of PCT/KR2003/002938 filed 31 Dec. 2003, which claims priority of Korean Patent Application No. 10-2003-0005058 filed 25 Jan. 2003.

TECHNICAL FIELD

The present invention relates to a method and apparatus for receiving data in a human body communication system that can improve the quality of received information and grasp the position information of a sensor in the human body by using plural receiving electrodes.

BACKGROUND ART

Various sensors for collecting medical information in the human body have been developed and used, herein, not only a technique for collecting information in the human body but also a technique for transmitting collected information to the outside of the human body are very important.

In a general data transmitting method, there is a communication cable method applied to an endoscope developed for observing the stomach and intestines. In the communication cable method, a cable made of a conducting wire or an optic fiber is inserted into the human body through throat of a patient. The communication cable method has high reliability and high data quality, however, a patient may suffer from severe pain during an endoscope operation.

In order to solve the above-mentioned problem, Given Imaging LTD. in Israel has developed a capsule type endoscope called M2A. When a patient swallows the capsule type endoscope like a tablet, image data in the human body photographed by a camera of the endoscope is transmitted to a receiving unit located outside the human body, and then displayed in a monitor.

However, because the M2A employs a radio wave method as a signal transmitting method, power consumption is increased, an operational time is reduced, and receiving sensitivity is deteriorated due to interference of various electric waves from the outside of the human body. In addition, because the M2A requires a radio transmitter such as a converter circuit for converting an image signal into a high frequency and an antenna for signal transmission, a volume is increased and production cost is high, and also the high frequency may be harmful to the human body. Accordingly, the present applicant has developed a human body communication system capable of transmitting data about the inside of the human body to the outside of the human body with a low frequency current by using the human body as a conductor.

In the human body communication system, an electric potential difference between transmitting electrodes that are formed on the surface of the capsule type endoscope put in the human body generates a current. As the current flows through the human body, it induces the voltage between two receiving electrodes installed on the surface of the human body, and accordingly a receiving apparatus can receive data regarding the inside of the human body.

FIG. 1 shows a human body communication system including a capsule type endoscope and two receiving electrodes. As depicted in FIG. 1, a capsule type endoscope 10 is located inside the human body 1, and a receiving apparatus 20 is located outside the human body. A transmitting electrode 11 is formed on the surface of both ends of the capsule type endoscope 10, and the receiving apparatus 20 is connected with two receiving electrodes 30 contacted to the surface of the human body. After medical information collected by the capsule type endoscope 10 is signal-processed, when electric potential difference occurs between the two transmitting electrodes 11, a current flows through the human body 2 since the two transmitting electrodes 11 are contacted with each other through body fluids and form a closed-loop. The current flowing on the surface of the human body induces a voltage between the two receiving electrodes 30 installed on the surface of the human body. The induced voltage is in proportion to the current and distance between the two receiving electrodes 30. The receiving apparatus 20 located outside the human body senses a signal transmitted from the capsule type endoscope 10 in the human body by the induced voltage.

However, when only the two receiving electrodes are used, if a direction of the current is vertical to an aligning direction of the receiving electrodes, voltage is not induced or a small amount of voltage is induced in the receiving electrodes. Accordingly, the receiving apparatus outside the human body may not receive accurately a signal transmitted from the capsule type endoscope in the human body.

In more detail, as illustrated in FIG. 1, when the capsule type endoscope 10 is located in an (A) direction, the aligning direction of the two receiving electrodes 30 is coincided with the direction of the transmitting electrode 11. In this case, a maximum current flows between the two receiving electrodes 30, so that the receiving apparatus 20 obtains good receiving sensitivity. However, when the capsule type endoscope 10 is located in a (B) direction, the aligning direction of the two receiving electrodes 30 is vertical to the direction of the transmitting electrode 11. In this case, a current does not flow between the two receiving electrodes 30, so that the receiving apparatus 20 can not receive a signal transmitted from the capsule type endoscope 10. Briefly, because the receiving electrode 30 is fixed and aligning direction of the transmitting electrode 11 is varied at any time, receiving sensitivity is varied as time elapses, a transmitted signal may be lost, and accordingly quality of receiving information is lowered.

In addition, when only the two receiving electrodes are used, position of the capsule type endoscope in the human body can not be detected, and accordingly the capsule type endoscope can not be used efficiently. For example, if we know a current position of the capsule type endoscope when the capsule type endoscope catches an abnormal symptom in the digestive organs, an accurate operation and remedy can be performed.

TECHNICAL GIST OF THE PRESENT INVENTION

In order to solve the above-mentioned problems, it is an object of the present invention to provide a method and apparatus for receiving data in a human body communication system, which are capable of receiving data with optimum sensitivity and extracting position information of a capsule type endoscope in the human body to use the position information as medical information.

In order to achieve the above-mentioned object, a method for receiving data in a human body communication system in accordance with the present invention comprise the steps of: selecting a pair of receiving electrodes sequentially among plural receiving electrodes; processing a voltage value of the selected pair of receiving electrodes and storing it in a memory; performing a predetermined operations for values stored in the memory to select an optimum pair of receiving electrodes; and performing image processing for a value corresponding to the optimum pair of receiving electrodes among the values stored in the memory.

In addition, an apparatus for receiving data in a human body communication system in accordance with the present invention comprises plural receiving electrodes installed on the surface of the human body; a switching means for selecting a pair of receiving electrodes sequentially among the plural receiving electrodes; a processing means for processing a voltage value of a pair of receiving electrode selected by the switching means; a memory for storing the processed value; a comparing-operating means for calculating a maximum value among values stored in the memory; an image processing means for performing image processing for the maximum value; and a control means for controlling the switching means and the comparing-operating means to provide the maximum value to the image processing means.

BRIEF DESCRIPTION OF DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE INVENTION

Hereinafter, the preferred embodiment of the present invention will be described with reference to accompanying drawings.

Figure 1:
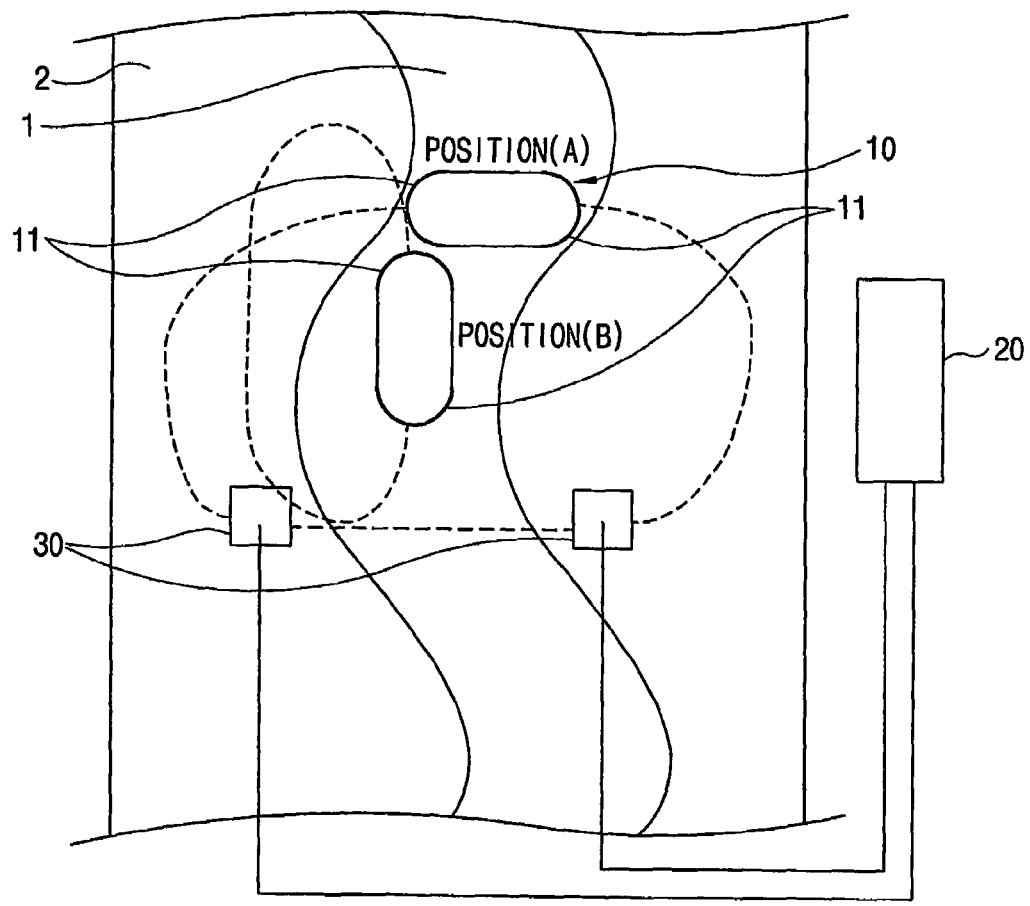
FIG. 1 is a diagram for showing problems occurred in data receiving in the conventional human body communication system.
Figure 2:
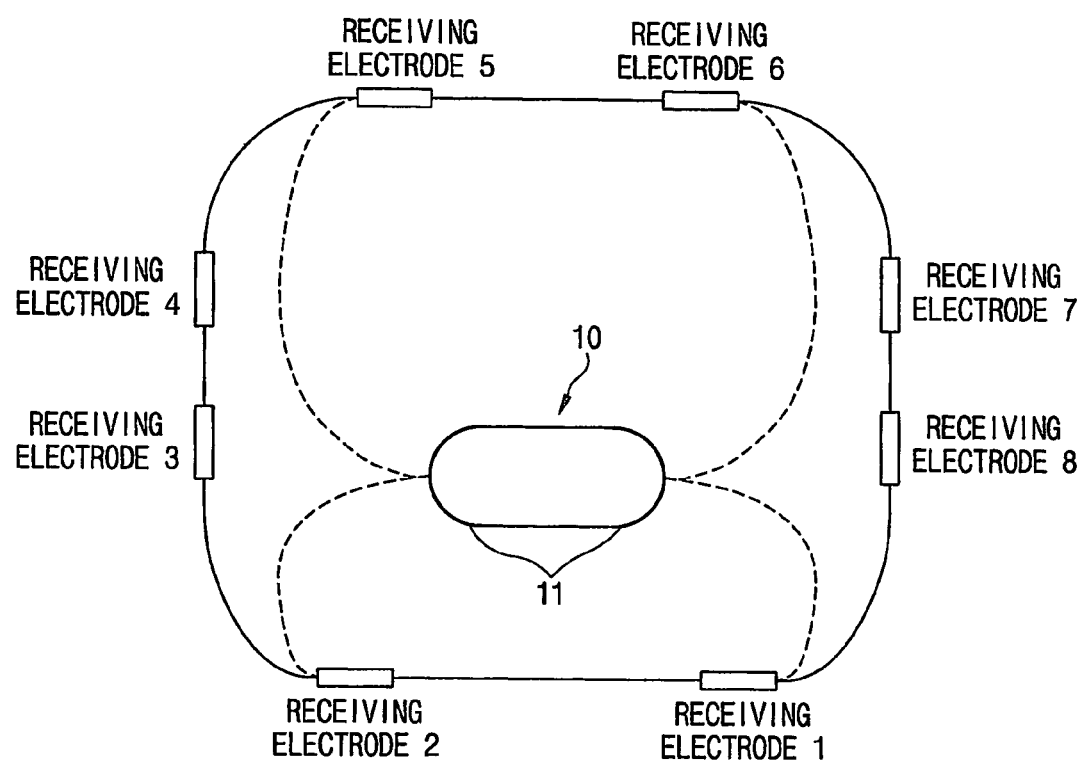
FIG. 2 is an exemplary view illustrating plural receiving electrodes installed on the surface of the human body in accordance with the present invention.

FIG. 2 is a plane view illustrating plural receiving electrodes installed on the surface of the human body. As depicted in FIG. 2, eight receiving electrodes are respectively installed on the surface of the human body, for example, the chest, the navel, an upper portion of the back, a lower portion of the back, the axillae and the sides. When current generated by electric potential difference between transmitting electrodes 11 of a capsule type endoscope 10 reaches plural receiving electrodes through the human body, a voltage is induced between the two receiving electrodes in proportion to the current and distance between the two receiving electrodes.

With reference to FIG. 2, considering receiving electrodes 1 and 2 as a pair of receiving electrodes, the greatest voltage is detected between receiving electrodes 1 and 2. That is because an aligning direction of the transmitting electrode 11 is coincided with that of the receiving electrodes 1 and 2 and also distance between the capsule type endoscope 10 and the receiving electrodes is the shortest. On the other hand, considering receiving electrodes 3 and 4 or receiving electrodes 7 and 8 as a pair of receiving electrodes, a voltage is not detected between the receiving electrodes. That is because an aligning direction of the transmitting electrode 11 of the capsule type endoscope 10 is vertical to an aligning direction of the receiving electrodes. In addition, considering receiving electrodes 5 and 6 as a pair of receiving electrodes, voltage between the receiving electrodes 5 and 6 is less than that between the receiving electrodes 1 and 2. That is because an aligning direction of the transmitting electrode 11 of the capsule type endoscope 10 is coincided with an aligning direction of the receiving electrodes, but distance between the capsule type endoscope 10 and the receiving electrodes 5 and 6 is farther than that between the capsule type endoscope 10 and the receiving electrodes 1 and 2.

As described-above, by measuring and comparing voltages between each pair of receiving electrodes, we select the receiving electrodes 1 and 2 to obtain better receiving sensitivity from the fact that the voltage between the receiving electrodes 1 and 2 is the greatest. In addition, we know the capsule type endoscope is located closer to the receiving electrodes 1 and 2 from the fact that a voltage of the receiving electrodes 1 and 2 is greater than that of the receiving electrodes 5 and 6.

An accurate position of the capsule type endoscope 10 in the human body can be extracted by comparing and operating voltages sensed in each pair of receiving electrodes at predetermined time-intervals. Also, a moving path, speed and direction, etc. of the capsule type endoscope in the human body can be known by processing an extracted position of the capsule type endoscope 10 sequentially.

In the embodiment of the present invention, flat-arranged plural receiving electrodes are described, however, the present invention is not limited by that. It is possible to extract three-dimensional position and direction of the capsule type endoscope 10 by distributing plural receiving electrodes onto the up/down, front/back and left/right of the human body.

Figure 3:
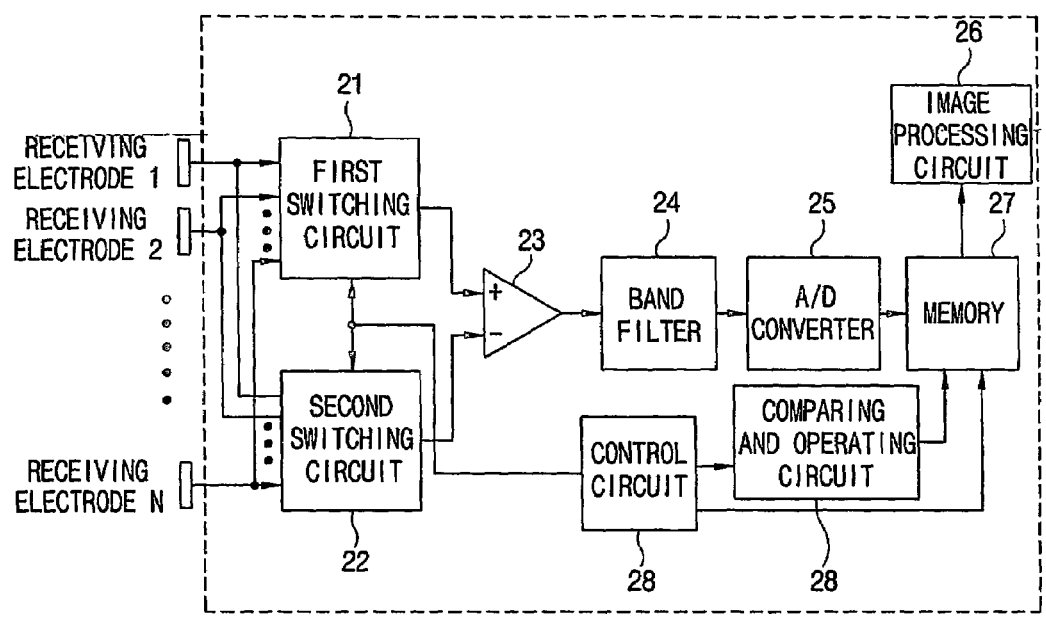
FIG. 3 is a block diagram illustrating a receiving apparatus in accordance with the present invention.

FIG. 3 is a block diagram illustrating a receiving apparatus having plural receiving electrodes in accordance with the present invention. As depicted in FIG. 3, N receiving electrodes are respectively connected to a first switching circuit 21 and a second switching circuit 22 of a receiving apparatus 30. An output line of the first switching circuit 21 is connected to a plus (+) terminal of a differential amplifier 23, and an output line of the second switching circuit 22 is connected to a minus (−) terminal of the differential amplifier 23. Under the control of a control circuit 28, the switching circuits 22, 23 respectively select only one among inputs from the N receiving electrodes.

The operation of the receiving apparatus 30 will be described in detail. First, when the first switching circuit 21 selects the receiving electrode 1 and the second switching circuit 22 selects the receiving electrode 2, a signal voltage between the receiving electrodes 1 and 2 is transmitted to the differential amplifier 23 to be amplified. The amplified signal passes a band pass filter 24 where noise is removed. The signal passing the band pass filter 24 is converted into a digital signal in an A/D converter 25 and is stored in a memory 27. Next, as the first switching circuit 21 maintains the receiving electrode 1, the second switching circuit 22 selects the receiving electrode 3. And then a signal voltage between the receiving electrodes 1 and 3 is stored in a different address of the memory 27 through the above-mentioned process. Continuously, as the first switching circuit 21 maintains the receiving electrode 1, the second switching circuit 22 selects the receiving electrode 4, 5, . . . and N, and then signal voltages between the receiving electrode 1 and the other receiving electrodes are sequentially stored in the memory 27.

Likewise, as the first switching circuit 21 maintains selection of the receiving electrode 2, the second switching circuit 22 selects the other receiving electrodes 1, 3, . . . and N sequentially, and then signal voltages between the receiving electrode 2 and the other receiving electrodes are sequentially stored in the memory 27. As described above, if the first switching circuit 21 selects the receiving electrode 3, 4, . . . and N sequentially and the second switching circuit 22 selects the other receiving electrodes sequentially, finally the $(N-1)^2$ number of signal voltages are stored in the memory 27. Of course, signal voltages between the receiving electrodes may be sampled several times (more than two times) for an average value to be stored. Or, an average value of a voltage waveform for a certain time may be stored. In addition, in order to reduce memory capacity and processing time, once-selected pair of receiving electrodes is no longer selected and the only $_nC_2$ number of a pair of receiving electrodes may be selected.

A comparing-operating circuit 29 compares signal voltage values stored in the memory 27 and obtains the greatest value. From that result of the comparing-operating circuit 29, it can be known a direction of the capsule type endoscope 10 is similar to an aligning direction of the pair of receiving electrodes in which the greatest value occurs. In addition, the comparing-operating circuit 29 may extract a three-dimensional position of the capsule type endoscope 10 by comparing and operating signal voltage values stored in the memory 27 and store it again in the memory 27.

The control circuit 28 selects the pair of receiving electrodes in which the greatest voltage occurs as communication electrodes, and accordingly a signal transmitted from the capsule type endoscope 10 in the human body can be received with the best receiving sensitivity. In more detail, a signal of the pair of receiving electrodes in which the greatest receiving voltage occurs is processed in an image processing circuit 26.

The above-described a pair of receiving electrodes combining procedure, signal voltage processing procedure, comparing-operating procedure and optimum pair of receiving electrodes selecting procedure, etc. are proceeded at a very quick speed (within 10 msec) and repeated at regular time-intervals (per 5 seconds). Accordingly, information transmitted from the capsule type endoscope 10 can be always received through an optimum pair of receiving electrodes. In addition, a moving path, a speed and a direction of the capsule type endoscope 10 in the human body can be measured by storing calculated position information in the memory 27 sequentially.

INDUSTRIAL APPLICABILITY

In the present invention, information transmitted from a capsule type endoscope using the human body as a communication conductor can be received with optimum receiving sensitivity to a receiving apparatus having plural receiving electrodes. Accordingly, it is possible to improve quality of received information, grasp a moving path, a speed and a direction of the capsule type endoscope in the human body and use them as medical information.

The invention claimed is:

1. A method for receiving data in a human body communication system, comprising the steps of:
    selecting a pair of receiving electrodes from among plural receiving electrodes placed on the surface of the human body;
    processing a voltage value sensed by and induced at the selected pair of receiving electrodes and storing it in a memory, wherein the voltage is induced by a current flowing in the human body, the current being generated by an electric potential difference between spaced transmitting electrodes located inside the human body;
    repeating the selecting and processing steps for at least an additional pair of receiving electrodes;
    performing predetermined operations for values stored in the memory to select an optimum pair of receiving electrodes; and
    performing image processing for a value corresponding to the optimum pair of receiving electrodes among the values stored in the memory.

2. The method of claim 1, wherein the step of processing the voltage comprises the sub-steps of:
    amplifying the voltage value;
    removing noise in the amplified signal; and
    converting the noise-removed analog signal into a digital signal.

3. The method of claim 1, wherein the values stored in the memory are averages of voltage values sampled more than two times or averages of voltage waveforms for a given time.

4. The method of claim 1, wherein a pair of receiving electrodes corresponding to a maximum value among the values stored in the memory is selected as the optimum pair of receiving electrodes.

5. The method of claim 1, further comprising the step of:
    calculating position information of a sensor from the position of the optimum pair of receiving electrodes and storing it in the memory sequentially.

6. The method of claim 5, wherein a moving path, a speed and a direction of the sensor are extracted from the position information.

7. An apparatus for receiving data in a human body communication system using plural receiving electrodes installable on the surface of the human body, the apparatus comprising:
    a switching device for selecting a pair of receiving electrodes from among the plural receiving electrodes;
    a processor for processing a voltage value induced at the pair of receiving electrodes selected by the switching device, wherein the voltage is induced by a current flowing in the human body, and the current is generated by an electric potential difference between two transmitting electrodes located inside the human body;
    a memory for storing voltage values;
    a comparator for determining a maximum value among the values stored in the memory;
    an image processor for performing image processing of data corresponding to an optimum pair of receiving electrodes associated with the maximum value; and
    a control for controlling the switching device and the comparator.

8. The apparatus of claim 7, wherein the switching device includes a first switching circuit and a second switching circuit to which the plural receiving electrodes are connected respectively.

9. The apparatus of claim 7, wherein the processor includes:
    a differential amplifier for amplifying a voltage output from the switching device;
    a band pass filter for removing noise in the amplified signal; and
    an A/D converter for converting the noise-removed analog signal into a digital signal.

10. The apparatus of claim 7, wherein the values stored in the memory are averages of voltage values sampled more than two times or are averages of voltage waveforms for a given time.

11. The apparatus of claim 7, wherein the comparator is operable to calculate position information of a sensor from the position of a pair of receiving electrodes corresponding to the maximum value and store the position information in the memory sequentially.

12. The apparatus of claim 11, including a further processor operable to extract a moving path, a speed and a direction of the sensor from the position information.

* * * * *